United States Patent
Yasukochi et al.

(10) Patent No.: US 10,806,705 B2
(45) Date of Patent: *Oct. 20, 2020

(54) ASENAPINE-CONTAINING PATCH

(71) Applicant: HISAMITSU PHARMACEUTICAL CO., INC., Tosu-shi, Saga (JP)

(72) Inventors: Takashi Yasukochi, Tsukuba (JP); Atsushi Sonobe, Tsukuba (JP); Satoshi Amano, Tsukuba (JP)

(73) Assignee: HISAMITSU PHARMACEUTICAL CO., INC., Tosu-Shi, Saga (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/745,266

(22) PCT Filed: Jul. 21, 2016

(86) PCT No.: PCT/JP2016/071451
§ 371 (c)(1),
(2) Date: Jan. 16, 2018

(87) PCT Pub. No.: WO2017/018322
PCT Pub. Date: Feb. 2, 2017

(65) Prior Publication Data
US 2019/0000775 A1 Jan. 3, 2019

(30) Foreign Application Priority Data
Jul. 27, 2015 (JP) .................. 2015-147518

(51) Int. Cl.
*A61K 47/18* (2017.01)
*A61K 9/70* (2006.01)
*A61K 31/407* (2006.01)
*A61K 47/14* (2017.01)

(52) U.S. Cl.
CPC .......... *A61K 9/7061* (2013.01); *A61K 9/7053* (2013.01); *A61K 9/7069* (2013.01); *A61K 31/407* (2013.01); *A61K 47/14* (2013.01); *A61K 47/18* (2013.01)

(58) Field of Classification Search
CPC ........ A61K 38/09; A61K 47/12; A61K 47/44; A61K 9/0034; A61K 9/02
See application file for complete search history.

(56) References Cited

U.S. PATENT DOCUMENTS

| 2008/0003273 | A1* | 1/2008 | Feldkamp | A61K 9/0014 424/448 |
| 2013/0053357 | A1 | 2/2013 | Kuma et al. | |
| 2015/0164862 | A1 | 6/2015 | Suzuki et al. | |
| 2015/0202183 | A1 | 7/2015 | Suzuki et al. | |
| 2015/0231250 | A1 | 8/2015 | Sonobe et al. | |

FOREIGN PATENT DOCUMENTS

| CN | 104487071 A | 4/2015 | |
| CN | 104487071 A * | 4/2015 | ........... A61K 9/7046 |
| EP | 2878299 A1 | 6/2015 | |
| EP | 3329914 A1 | 6/2018 | |
| EP | 3357945 A1 | 8/2018 | |
| KR | 1020130029034 A | 3/2013 | |
| KR | 1020150036477 A | 4/2015 | |
| KR | 1020150036478 A | 4/2015 | |
| KR | 1020150036479 A | 4/2015 | |
| TW | 201410270 A | 3/2014 | |
| WO | 2005046653 A1 | 5/2005 | |
| WO | WO-2005046653 A1 * | 5/2005 | ........... A61K 31/192 |
| WO | WO-2008107347 A2 * | 9/2008 | ............... A61K 8/35 |
| WO | 2010/127674 A1 | 11/2010 | |
| WO | WO-2010127674 A1 * | 11/2010 | ............... A61K 9/06 |
| WO | 2011/136283 A1 | 11/2011 | |
| WO | 2014/017593 A1 | 1/2014 | |
| WO | 2014/017594 A1 | 1/2014 | |
| WO | 2014/017595 A1 | 1/2014 | |

OTHER PUBLICATIONS

Trenor et al. Journal of Materials Science Letters 21, 2002, 1321-1323). (Year: 2002).*
Cilurzo et al. (Francesco Cilurzo, Chiara G M Gennari & Paola Minghetti (2012) Adhesive properties: a critical issue in transdermal patch development, Expert Opinion on Drug Delivery, 9:1, 33-45) (Year: 2012).*
"Handbook of pressure sensitive adhesive technology", The Nikkan Kogyo Shinbun, Ltd., 1st edition, 1st print, Mar. 31, 1997., p. 559-p. 569, Abstract Attached.
International Search Report dated Sep. 13, 2016 corresponding to application No. PCT/JP2016/071451.
International Preliminary Report on Patentability (IPRP) dated Feb. 8, 2018 in corresponding the WO Patent Application No. PCT/JP2016/071451.
Office Action dated Feb. 8, 2019 corresponding to Korean application No. 10-2018-7001122.
Database WPI; Week 201176; Thomson Scientific, London, GB; AN 2011-N64518; XP002788834; Nov. 3, 2011.
The extended European Search Report dated Feb. 26, 2019 corresponding to application No. 16830427.7.
Office Action dated Apr. 18, 2019 corresponding to Taiwan application No. 105123612.
Decision for Grant of Patent dated Jun. 27, 2019 corresponding to Korean Patent Application No. 10-2018-7001122.
Chinese Office Action dated Apr. 1, 2020 corresponding to application No. 201680043630.4.

* cited by examiner

*Primary Examiner* — Ernst V Arnold
(74) *Attorney, Agent, or Firm* — Nath, Goldberg & Meyer; Joshua B. Goldberg

(57) ABSTRACT

The present invention provides a patch comprising a backing and an adhesive layer laminated on one side of the backing, wherein the adhesive layer comprises asenapine or a pharmaceutically acceptable salt thereof, an adhesive base and a low molecular weight amine.

2 Claims, 2 Drawing Sheets

ASENAPINE-CONTAINING PATCH

This is a National Phase Application filed under 35 U.S.C. 371 as a national stage of PCT/JP2016/071451, filed Jul. 21, 2016, an application claiming the benefit of Japanese Application No. 2015-147518, filed Jul. 27, 2015, the content of each of which is hereby incorporated by reference in its entirety.

TECHNICAL FIELD

The present invention relates to an asenapine-containing patch.

BACKGROUND ART

Asenapine is a compound known as a therapeutic agent of central nervous system diseases, in particular, schizophrenia. A patch containing asenapine is described in, for example, Patent Literature 1 to 4. A patch containing free asenapine is known to be excellent in the skin permeability of asenapine.

CITATION LIST

Patent Literature

Patent Literature 1: WO 2010/127674
Patent Literature 2: WO 2014/017593
Patent Literature 3: WO 2014/017594
Patent Literature 4: WO 2014/017595

SUMMARY OF INVENTION

Technical Problem

The present inventors have found that the adhesive layer of a patch absorbs moisture due to contact with sweat etc. secreted from skin, exposure to moisture in air, and contact with water and vapor in activities of daily living such as bathing and cooking and its adhesion may be reduced. Such reduction of the adhesion is remarkable when the patch is patched for a long time. Also, when the patch is stored for a long time, the adhesive layer absorbs moisture and the adhesion may be reduced.

Thus, an object of the present invention is to provide a patch in which the reduction of the adhesion is inhibited even when the adhesive layer absorbs moisture.

Solution to Problem

As a result of intensive investigation, the present inventors have found that in an asenapine-containing patch the adhesiveness of an adhesive layer containing a low molecular weight amine is maintained even when the adhesive layer absorbs moisture, thereby completing the present invention.

Namely, the present invention provides a patch comprising a backing and an adhesive layer laminated on one side of the backing, wherein the adhesive layer contains asenapine or a pharmaceutically acceptable salt thereof, an adhesive base and a low molecular weight amine. It is preferable that the low molecular weight amine in the patch be one or more selected from the group consisting of monoethanolamine, diethanolamine, triethanolamine, isopropanolamine and diisopropanolamine.

The present invention also provides a method of inhibiting the reduction of the adhesion in a patch comprising a backing and an adhesive layer laminated on one side of the backing due to the moisture absorption of the adhesive layer, comprising: forming the adhesive layer from an adhesive composition obtained by mixing asenapine or a pharmaceutically acceptable salt thereof, an adhesive base and a low molecular weight amine.

Advantageous Effects of Invention

With the adhesive related to the present invention, the reduction of the adhesion of the adhesive layer is inhibited even after the adhesive layer absorbed moisture. In particular, it is thought that a silicone adhesive base is susceptible to sweating etc. of users because the hydrophilicity of a silicone adhesive base is poorer than other adhesive bases. In fact, in a patch containing a silicone adhesive base, the rate of reduction of the adhesion due to moisture absorption of the adhesive layer is remarkable and is higher compared to that of a patch containing an acrylic adhesive base. The ratio of reduction of the adhesion due to moisture absorption of the adhesive layer in a patch containing an acrylic adhesive base is higher compared to that of a patch containing a rubber adhesive base. According to the present invention, the reduction of the adhesion due to moisture absorption can be inhibited in a patch containing any adhesive base of a silicone adhesive base, an acrylic adhesive base and a rubber adhesive base.

DESCRIPTION OF EMBODIMENTS

Figure 1:
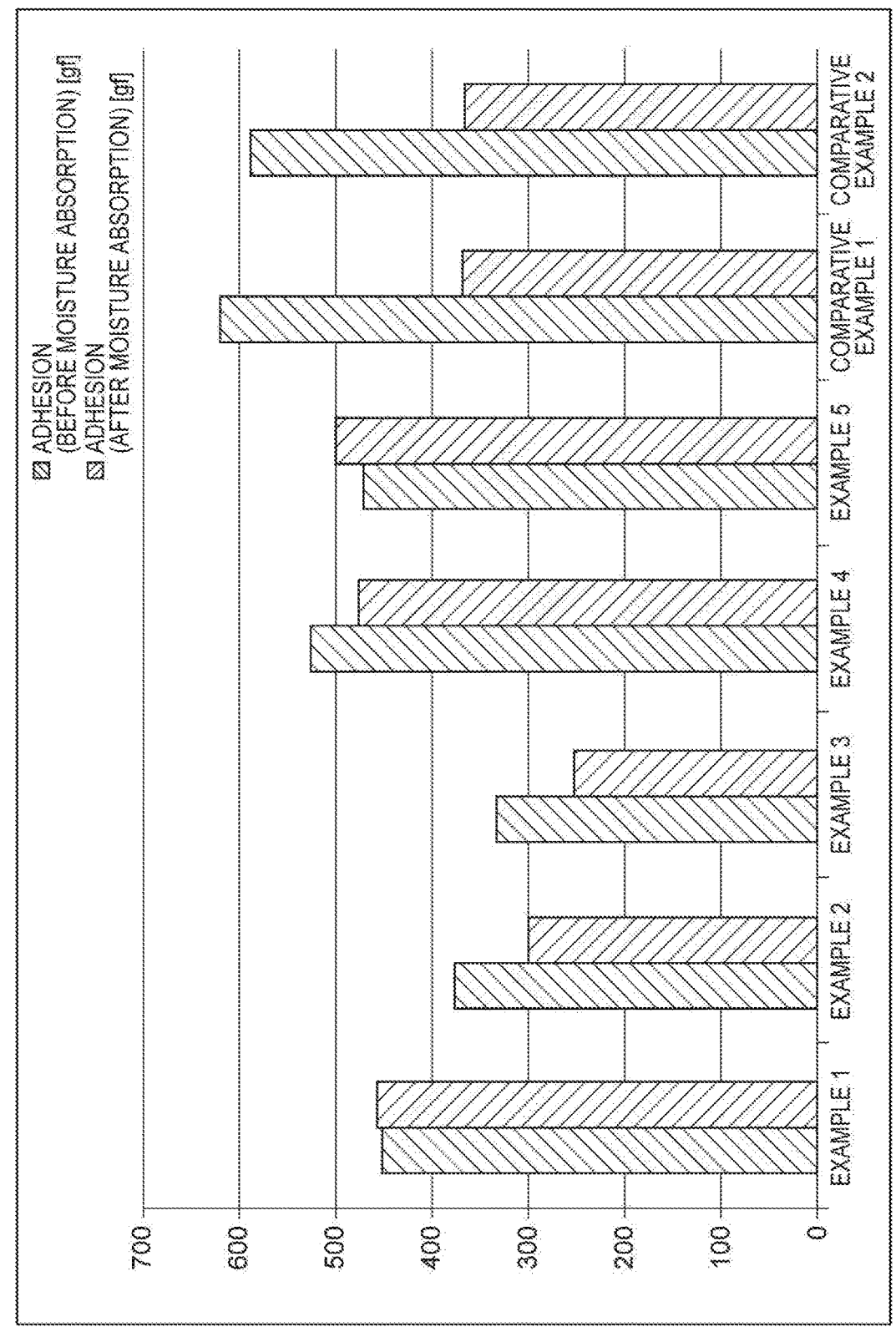
FIG. 1 is a graph showing the change in adhesion due to moisture absorption.

The present invention will be described in detail below with showing embodiments of the present invention.

One embodiment of the present invention is a patch comprising a backing and an adhesive layer laminated on the backing. The patch is a patch comprising a backing and an adhesive layer laminated on one side of the backing, wherein the adhesive layer contains asenapine or a pharmaceutically acceptable salt thereof, an adhesive base and a low molecular weight amine.

The backing may be any backing which can maintain the form of the patch, in particular, the adhesive layer. Examples of the material of the backing include polyethylene, polypropylene, polybutadiene, an ethylene-vinyl chloride copolymer, polyvinyl chloride, polyamide such as nylon (trade name), polyester, a cellulose derivative, and a synthetic resin such as polyurethane. Examples of the shape of the backing include a film, a sheet, a sheet-like porous body, sheet-like foam, fabric such as woven fabric, knitted fabric and nonwoven fabric, and laminated products thereof. The thickness of the backing is not specifically limited, but it is preferable that the thickness of the backing be normally about 2 to 3000 μm.

The adhesive layer contains asenapine or a pharmaceutically acceptable salt thereof, an adhesive base and a low molecular weight amine.

The thickness of the adhesive layer is not specifically limited and may be 30 to 300 μm. If the thickness of the adhesive layer is over 300 μm, the patch tends to easily fall off, for example when clothes are put on or off.

Asenapine is a compound which is also referred to as (3aRS,12bRS)-5-chloro-2-methyl-2,3,3a,12b-tetrahydro-1H-dibenzo[2, 3:6,7]oxepino[4,5-c]pyrrole and is represented by the following formula (1). Asenapine has a plurality of optical isomers and may be any optical isomer, and may be a mixture of optical isomers such as a racemate. The acid added to asenapine is not specifically limited as long as it is pharmaceutically acceptable. Examples of the acid include hydrochloric acid, hydrobromic acid, hydroiodic acid, phosphoric acid, acetic acid, propionic acid, glycolic acid, maleic acid, malonic acid, succinic acid, tartaric acid, citric acid, ascorbic acid, salicylic acid and benzoic acid. The acid addition salt of asenapine may be anhydride or hydrate. For example, asenapine maleate is commercially available as a therapeutic agent of schizophrenia.

[Chemical Formula 1]

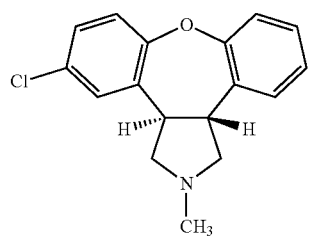
(1)

The low molecular weight amine is an amine whose molecular weight is 30 to 300 and may be a compound represented by the formula (2).

[Chemical Formula 2]

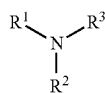
(2)

The low molecular weight amine is a compound represented by the formula (2), wherein $R^1$, $R^2$ and $R^3$ are each independently a hydrogen atom, an optionally substituted alkyl group (preferably, an alkyl group having 1 to 12 carbon atoms) or an optionally substituted aryl group (preferably, an aryl group having 6 to 14 carbon atoms). Any two or three of $R^1$, $R^2$ and $R^3$ may bond directly each other to form a heterocycle structure, or any two or three bond each other through an oxygen atom, a sulfur atom or an imino group (—$NR^4$—) to form a heterocycle structure. $R^4$ is a hydrogen atom, an optionally substituted alkyl group (preferably, an alkyl group having 1 to 12 carbon atoms) or an optionally substituted aryl group (preferably, an aryl group having 6 to 14 carbon atoms). Here, "optionally substituted" means that the group is further substituted by a substituent such as a hydroxy group, an amino group and a thiol group. It is preferable that the total number of carbon atoms of $R^1$, $R^2$ and $R^3$ be 12 or less.

Examples of the low molecular weight amine include ammonia and linear or branched alkylamines such as monoethylamine, diethylamine, propylamine, dipropylamine, triethylamine and diisopropylethylamine; alkanolamines such as monoethanolamine, diethanolamine, triethanolamine, monoisopropanolamine, diisopropanolamine, trometamol, ethylenediamine and meglumine; diamines such as ethylenediamine; cyclic amines such as pyrrolidine, piperidine, morpholine, piperazine and quinuclidine; arylamines such as aniline. It is preferable that the low molecular weight amine be one or more selected from the group consisting of monoethanolamine, diethanolamine, triethanolamine, isopropanolamine and diisopropanolamine.

The adhesive base is a component which gives adhesiveness to an adhesive layer, and examples of the adhesive base include a rubber adhesive base, an acrylic adhesive base and silicone adhesive base. It is preferable that the adhesive base be one or more selected from the group consisting of a rubber adhesive base, an acrylic adhesive base and a silicone adhesive base. It is preferable that the adhesive base be free of water (a nonaqueous adhesive base). It is preferable that the total content of the adhesive base be 40 to 98% by mass relative to the total mass of the adhesive layer, and it is more preferable that the total content of the adhesive base be 50 to 95% by mass.

Examples of the rubber adhesive base include natural rubber, polyisobutylene, an alkyl vinyl ether (co)polymer, polyisoprene, polybutadiene, styrene-butadiene copolymer, styrene-isoprene copolymer and a styrene-isoprene-styrene block copolymer, and one of these may be used alone or two or more may be used in combination. Among these, it is preferable that the rubber adhesive related to the present invention be at least one selected from the group consisting of a styrene-isoprene-styrene block copolymer and polyisobutylene, and it is more preferable that the rubber adhesive related to the present invention be a styrene-isoprene-styrene block copolymer and polyisobutylene, from the viewpoints that the releasing properties of asenapine from the adhesive layer are more improved and that it tends to be possible to achieve more sufficient adhesion of the adhesive layer. Here, it is specifically preferable that the mass ratio of a styrene-isoprene-styrene block copolymer to polyisobutylene (a styrene-isoprene-styrene block copolymer:polyisobutylene) be 15:2 to 2:15.

Specific examples of the rubber adhesive base include a styrene-isoprene-styrene block copolymer (SIS), isoprene rubber, polyisobutylene (PIB), a styrene-butadiene-styrene block copolymer (SBS) and styrene-butadiene rubber (SBR). One of these rubber adhesives may be used alone or two or more may be used in combination. Examples of the preferred rubber adhesive include SIS and PIB. Specific examples of the rubber adhesive include Oppanol B12, B15, B50, B80, B100, B120, B150 and B220 (trade name, manufactured by BASF), JSR BUTYL 065, 268 and 365 (trade name, manufactured by JSR Corporation), Vistanex LM-MS, MH, H, MML-80, 100, 120 and 140 (trade name, manufactured by Exxon Chemicals), HYCAR (trade name, manufactured by Goodrich Corporation), and SIBSTAR T102 (trade name, manufactured by Kaneka Corporation).

The content of the rubber adhesive base is 0 to 98% by mass relative to the total mass of the adhesive layer, and it is preferable that the content of the rubber adhesive base be 0 to 85% by mass.

The acrylic adhesive base is a component which gives adhesiveness to an adhesive layer, and examples of the acrylic adhesive base include (co)polymers of one or two or more types of (meth)acrylic acid alkyl ester. Examples of the (meth)acrylic acid alkyl ester include butyl (meth)acrylate, isobutyl (meth)acrylate, hexyl (meth)acrylate, octyl (meth)acrylate, 2-ethylhexyl (meth)acrylate and decyl (meth)acrylate. In the specification, the term "(meth)acrylic acid" refers to either one or both of acrylic acid and methacrylic acid, and similar expressions are defined in a same manner.

The acrylic adhesive base may be a copolymer formed from (meth)acrylic acid alkyl ester (a main monomer) and a comonomer. Examples of the main monomer include methyl (meth)acrylate, ethyl (meth)acrylate, butyl (meth)acrylate, hexyl (meth)acrylate, heptyl (meth)acrylate, octyl (meth) acrylate and 2-ethylhexyl (meth)acrylate, and one of these may be used alone or two or more may be used in combination. The comonomer may be any component which can copolymerize with (meth)acrylic acid alkyl ester. Examples of the comonomer include (meth)acrylic acid hydroxyalkyl ester, ethylene, propylene, styrene, vinyl acetate, N-vinylpyrrolidone, (meth)acrylic acid and amide (meth)acrylate. One of these comonomers may be used alone or two or more may be used in combination.

Specific examples of the acrylic adhesive base include an acrylic acid-acrylic acid octyl ester copolymer, a 2-ethylhexyl acrylate-vinylpyrrolidone copolymer solution, an acrylic acid ester-vinyl acetate copolymer, a 2-ethylhexyl acrylate-2-ethylhexyl methacrylate-dodecyl methacrylate copolymer, a methyl acrylate-2-ethylhexyl acrylate copolymer resin emulsion, and an acrylic polymer contained in an acrylic resin alkanolamine solution. Specific examples of such acrylic adhesives include a series of DURO-TAK such as DURO-TAK (Registered trademark) 387-2510, DURO-TAK (Registered trademark) 87-2510, DURO-TAK (Registered trademark) 387-2287, DURO-TAK (Registered trademark) 87-2287, DURO-TAK (Registered trademark) 87-4287, DURO-TAK (Registered trademark) 387-2516, DURO-TAK (Registered trademark) 87-2516, DURO-TAK (Registered trademark) 87-2074, DURO-TAK (Registered trademark) 87-900A, DURO-TAK (Registered trademark) 87-901A, DURO-TAK (Registered trademark) 87-9301 and DURO-TAK (Registered trademark) 87-4098 (manufactured by Henkel); a series of GELVA such as GELVA (Registered trademark) GMS 788, GELVA (Registered trademark) GMS 3083 and GELVA (Registered trademark) GMS 3253 (manufactured by Henkel); a series of MAS such as MAS811 (trade name) and MAS683 (trade name) (manufactured by CosMED); a series of EUDRAGIT (Registered trademark, manufactured by Evonik Industries AG), NICAZOLE (Registered trademark, manufactured by NIPPON CARBIDE INDUSTRIES CO., INC.) and ULTRAZOLE (Registered trademark, manufactured by Aica Kogyo Co., Ltd.).

The content of the acrylic adhesive base is 0 to 98% by mass relative to the total mass of the adhesive layer, and it is preferable that the content of the acrylic adhesive base be 0 to 80% by mass.

The silicone adhesive base is a compound which has an organopolysiloxane backbone. Examples of the silicone adhesive base include dimethylpolysiloxane, polymethylvinylsiloxane and polymethylphenylsiloxane. Specific examples of the silicone adhesive base include a series of MD such as MD7-4502 Silicone Adhesive and MD7-4602 Silicone Adhesive (manufactured by Dow Corning); a series of BIO-PSA such as BIO-PSA (Registered trademark) 7-4301 Silicone Adhesive, BIO-PSA (Registered trademark) 7-4302 Silicone Adhesive, BIO-PSA (Registered trademark) 7-4201 Silicone Adhesive, BIO-PSA (Registered trademark) 7-4202 Silicone Adhesive, BIO-PSA (Registered trademark) 7-4101 Silicone Adhesive, BIO-PSA (Registered trademark) 7-4102 Silicone Adhesive, BIO-PSA (Registered trademark) 7-4601 Silicone Adhesive, BIO-PSA (Registered trademark) 7-4602 Silicone Adhesive, BIO-PSA (Registered trademark) 7-4501 Silicone Adhesive, BIO-PSA (Registered trademark) 7-4502 Silicone Adhesive, BIO-PSA (Registered trademark) 7-4401 Silicone Adhesive and BIO-PSA (Registered trademark) 7-4402 Silicone Adhesive (manufactured by Dow Corning), Dow Corning (Registered trademark) 7-9800A, Dow Corning (Registered trademark) 7-9800B, Dow Corning (Registered trademark) 7-9700A and Dow Corning (Registered trademark) 7-9700B.

The content of the silicone adhesive base is 0 to 98% by mass relative to the total mass of the adhesive layer, and it is preferable that the content of the silicone adhesive base be 0 to 85% by mass.

The adhesive layer may further contain other additives. Examples of the other additives include a tackifier resin, a plasticizer, a percutaneous absorption promoting agent, a stabilizing agent, a filler and a flavor.

The tackifier resin is a component which adjusts the adhesiveness of the adhesive layer. Examples of the tackifier resin include an alicyclic saturated hydrocarbon resin; rosin and rosin derivatives such as glycerine ester of rosin, hydrogenated rosin, glycerine ester of hydrogenated rosin, pentaerythritol ester of rosin and maleated rosin; a terpene tackifier resin; a petroleum tackifier resin. One of the tackifier resins may be used alone or two or more may be used in combination. It is preferable that the tackifier resin be an alicyclic saturated hydrocarbon resin in that it is excellent in drug-releasing properties.

When the adhesive layer contains the tackifier resin, it is preferable that the content of the tackifier resin be 0 to 80% by mass relative to the total mass of the adhesive layer, and it is more preferable that the content of the tackifier resin be 0 to 70% by mass. When the content of the tackifier resin is 80% by mass or less, the aggregability of the adhesive tends to be excellent.

The absorption promoting agent is a component which adjusts the skin permeability of asenapine or a pharmaceutically acceptable salt thereof. The absorption promoting agent is not specifically limited as long as it is a compound whose absorption promoting action to skin is conventionally recognized, and examples of the absorption promoting agent include an aliphatic alcohol having 6 to 20 carbon atoms, an aliphatic ether having 6 to 20 carbon atoms, a fatty acid having 6 to 20 carbon atoms, a fatty ester having 6 to 20 carbon atoms, a fatty acid amide having 6 to 20 carbon atoms, glycerine, glycerine fatty esters, propylene glycols, propylene glycol fatty esters, polyethylene glycol and polyethylene glycol fatty esters, an aromatic organic acid, an aromatic alcohol, an aromatic organic acid ester, an aromatic organic ether (the above compounds may be saturated or unsaturated, and may be linear or branched, and may comprise a cyclic structure), lactic acid esters, acetic acid esters, a monoterpenes compound, a sesquiterpene compound, Azone (Registered trademark), an Azone derivative, pyrrothiodecane, sorbitan fatty esters (a series of Span (Registered trademark)), a series of polysorbate (a series of Tween (Registered trademark)), polyoxyethylene hydrogenated castor oils, polyoxyethylene alkylethers, sucrose fatty acid esters and a plant oil. Specific examples of the absorption promoting agent include caprylic acid, capric acid, caproic acid, lauric acid, myristic acid, palmitic acid, stearic acid, isostearic acid, oleic acid, linoleic acid, linolenic acid, lauryl alcohol, myristyl alcohol, oleyl alcohol, isostearyl alcohol, cetyl alcohol, methyl laurate, hexyl laurate, diethanolamide laurate, isopropyl myristate, myristyl myristate, octyldodecyl myristate, cetyl palmitate, isopropyl palmitate, salicylic acid, methyl salicylate, ethylene glycol salicylate, cinnamic acid, methyl cinnamate, cresol, cetyl lactate, lauryl lactate, ethyl acetate, propyl acetate, geraniol, thymol, eugenol, terpineol, 1-menthol, borneoroll, d-limonene, isoeugenol, isoborneol, nerol, dl-camphor, glycerin monocaprylate, glycerin monocaprate, glycerine monolaurate, glycerine monooleate, sorbitan monolaurate, sucrose monolaurate, polysorbate 20, propylene glycol, propylene glycol monolaurate, polyethylene glycol monolaurate, polyethylene glycol monostearate, polyoxyethylene lauryl ether, NIKKOL (Registered trademark) HCO-60 (Nikko Chemicals Co., Ltd.), Pyrrothiodecane (Registered trademark), olive oil and sorbitan monooleate. One of the absorption promoting agents may be used alone or two or more may be used in combination. It is preferable that the absorption promoting agent be a fatty acid derivative in that it is superior in the absorptivity of asenapine.

When the adhesive layer contains the absorption promoting agent, it is preferable that the content of the absorption promoting agent be 0 to 30% by mass relative to the total mass of the adhesive layer, and it is more preferable that the content of the absorption promoting agent be 0 to 20% by mass. When the content of the absorption promoting agent is 30% by mass or less, the adhesiveness tends not to be reduced even after the moisture absorption.

Examples of the stabilizing agent include tocopherol and ester derivatives thereof, ascorbic acid and ester derivatives thereof, dibutylhydroxytoluene, butylhydroxyanisole, and 2-mercaptobenzimidazole. One of the stabilizing agents may be used alone or two or more may be used in combination. It is preferable that the stabilizing agent be dibutylhydroxytoluene in that it can inhibit the degradation of asenapine more.

When the adhesive layer contains the stabilizing agent, it is preferable that the content of the stabilizing agent be 0 to 5% by mass relative to the total mass of the adhesive layer, and it is more preferable that the content of the stabilizing agent be 0 to 3% by mass. When the content of the stabilizing agent is 5% by mass or less, the adhesiveness tends not to be reduced even after the moisture absorption.

The patch may further comprise a release liner. The release liner is laminated on the side opposite to the backing on the adhesive layer. When the patch comprises a release liner, the deposition of dirt etc. onto the adhesive layer tents to be reduced during storage.

The raw material of the release liner is not specifically limited, and liners generally known to those in the art may be used. Examples of the material of the release liner include polyester such as polyethylene terephthalate and polyethylene naphthalate; polyolefin such as polyethylene and polypropylene; films of polyvinyl chloride or polyvinylidene chloride etc.; laminated films of fine quality paper and polyolefin; films of Nylon (Registered trademark) or aluminium etc. It is preferable that the material of the release liner be polypropylene or polyethylene terephthalate.

Method of Manufacturing a Patch

The patch of the present invention can be manufactured, for example, by the following method. First, asenapine or a pharmaceutically acceptable salt thereof, an adhesive base and a low molecular weight amine are mixed, and a solvent and other additives etc. are added to the mixture and the mixture is mixed as needed to obtain a homogeneous adhesive composition. Then, the obtained adhesive composition is applied onto one side of a backing in a given thickness, and then is heated as needed to dry and remove the solvent, and the obtained sheet is cut into a desired size to obtain the patch. Heating conditions can be selected as appropriate depending on the solvent and it is preferable that temperature conditions be 60 to 120° C., and heating time is, for example, 2 to 30 minutes.

When a patch comprising a release liner is manufactured, an adhesive composition is applied to a backing, and the solvent is dried and removed, and then the release liner can be laminated. Also, when a patch comprising a release liner is manufactured, the patch can be obtained by applying an adhesive composition onto one side of the release liner in a given thickness, and then heating the composition as needed to dry and remove the solvent, and laminating a backing, and cutting the obtained sheet into a desired size.

The adhesive composition used in the method of manufacturing contains asenapine or a pharmaceutically acceptable salt thereof, an adhesive base and a low molecular weight amine, and may further contain a solvent and other additives etc. as needed.

The solvent may be a solvent which does not react with other components contained in the adhesive composition, and is added to adjust the viscosity of the adhesive composition. Examples of the solvent include toluene, ethanol, methanol and ethyl acetate. One of the solvent may be used alone or two or more may be used in combination. The content of the solvent may be adjusted in consideration of the viscosity of the adhesive composition.

It is preferable that the content of asenapine or a pharmaceutically acceptable salt thereof in the adhesive composition be 1 to 30% by mass relative to the total mass of the adhesive composition, and it is more preferable that the content of asenapine or a pharmaceutically acceptable salt thereof in the adhesive composition be 3 to 25% by mass.

It is preferable that the content of the adhesive base in the adhesive composition be 40 to 98% by mass relative to the total mass of the adhesive composition, and it is more preferable that the content of the adhesive base in the adhesive composition be 50 to 85% by mass. When the content of the adhesive base is 40% by mass or more, the reduction of the adhesion tends to be less even after the moisture absorption.

It is preferable that the content of the low molecular weight amine in the adhesive composition be 0.5 to 40% by mass relative to the total mass of the adhesive composition, and it is more preferable that the content of the low molecular weight amine in the adhesive composition be 1 to 30% by mass.

It is preferable that the content of other additives in the adhesive composition be 0 to 30% by mass relative to the total mass of the adhesive composition, and it is more preferable that the content of other additives in the adhesive composition be 0 to 20% by mass.

EXAMPLES

The present invention will be described in more detail below with showing Examples and Comparative Examples.

(1) Manufacturing of Patches

The components were mixed in the mass ratio described in Table 1 to prepare the rubber adhesive 1. The components described in Table 2 were each weighed out and solvents were added there as needed and the mixtures were mixed to obtain adhesive compositions. The obtained adhesive compositions were applied to polyester release liners and the solvents were dried and removed to form adhesive layers. Polyester films (backings) were laminated on the obtained adhesive layers and the obtained sheets were cut as appropriate to obtain desired patches. The figures in Table 2 refer to figures in % by mass.

TABLE 1

| | Rubber adhesive 1 |
|---|---|
| SIS | 70 |
| PIB | 30 |
| Tackifier resin | 290 |
| Liquid paraffin | 40 |

TABLE 2

| | Example 1 | Example 2 | Example 3 | Example 4 |
|---|---|---|---|---|
| Asenapine maleate | 4.5 | 4.5 | 4.5 | 4.5 |
| Rubber adhesive 1 | 82.8 | 80.8 | 78.8 | 82.1 |
| Isopropyl palmitate | 10 | 10 | 10 | 10 |
| Monoethanolamine | 2.7 | — | — | — |
| Diethanolamine | — | 4.7 | — | — |
| Triethanolamine | — | — | 6.7 | — |
| Isopropanolamine | — | — | — | 3.4 |
| Diisopropanolamine | — | — | — | — |
| Polyethylenimine | — | — | — | — |
| Sodium acetate | — | — | — | — |
| Total | 100 | 100 | 100 | 100 |

| | Example 5 | Comp. Example 1 | Comp. Example 2 |
|---|---|---|---|
| Asenapine maleate | 4.5 | 4.5 | 4.5 |
| Rubber adhesive 1 | 79.5 | 83.6 | 81.8 |
| Isopropyl palmitate | 10 | 10 | 10 |
| Monoethanolamine | — | — | — |
| Diethanolamine | — | — | — |
| Triethanolamine | — | — | — |
| Isopropanolamine | — | — | — |
| Diisopropanolamine | 6 | — | — |
| Polyethylenimine | — | 1.9 | — |
| Sodium acetate | — | — | 3.7 |
| Total | 100 | 100 | 100 |

(2) Measurement of Adhesion

For the adhesion of the obtained patches, with reference to the description in JIS Z0237: 1991, a stainless probe with a diameter of 5 mm was contacted with the adhesive layer for 1 second at a speed of 120 mm/min with a contact load of 200 gf/cm$^2$, and then the force required to peel at a speed of 120 mm/min (unit: gf) was measured and the maximums were described as adhesion (before moisture absorption) in Table 3.

The release liners of the patches were removed and the patches were allowed to stand for 48 hours under conditions of 40° C., 75% relative humidity. Then, the force required to peel was measured in the same way and the maximums were described as adhesion (after moisture absorption) in Table 3. "Rate of change (%)" in Table 3 refers to the value of adhesion of the adhesive layer after moisture adsorption when the value of adhesion of the adhesive layer before moisture absorption is taken as 100.

The result is shown in Table 3 and FIG. 1. The reduction of the adhesion of the patches of Examples 1 to 5 was less compared to that of the patches of Comparative Example 1 or 2 after the moisture absorption of the adhesive layers. In particular, the reduction of the adhesion of the patches of Examples 1, 4 and 5 was hardly observed.

TABLE 3

| | Example 1 | Example 2 | Example 3 | Example 4 |
|---|---|---|---|---|
| Adhesion (before moisture absorption) [gf] | 452 | 376 | 334 | 525 |
| Adhesion (after moisture absorption) [gf] | 457 | 302 | 252 | 476 |
| Rate of change [%] | 101 | 80 | 75 | 91 |

| | Example 5 | Comp. Example 1 | Comp. Example 2 |
|---|---|---|---|
| Adhesion (before moisture absorption) [gf] | 470 | 619 | 589 |
| Adhesion (after moisture absorption) [gf] | 500 | 368 | 363 |
| Rate of change [%] | 106 | 59 | 62 |

(3) Manufacturing of Patches

The components described in Table 4 were each weighed out and solvents were added there as needed and the mixtures were mixed to obtain adhesive compositions. The obtained adhesive compositions were applied to polyester release liners and the solvents were dried and removed to form adhesive layers. Polyester films (backings) were laminated on the obtained adhesive layers and the obtained sheets were cut as appropriate to obtain desired patches. The figures in Table 4 refer to figures in % by mass.

TABLE 4

| | Example 6 | Example 7 | Example 8 | Example 9 |
|---|---|---|---|---|
| Asenapine maleate | 21 | 21 | 21 | 21 |
| DURO-TAK 87-2516 | 66.2 | 57 | 47.8 | 63.3 |
| Monoethanolamine | 12.8 | — | — | — |
| Diethanolamine | — | 22 | — | — |
| Triethanolamine | — | — | 31.2 | — |
| Isopropanolamine | — | — | — | 15.7 |
| Diisopropanolamine | — | — | — | — |
| Sodium hydroxide | — | — | — | — |
| Sodium acetate | — | — | — | — |
| Total | 100 | 100 | 100 | 100 |

| | Example 10 | Comp. Example 3 | Comp. Example 4 |
|---|---|---|---|
| Asenapine maleate | 21 | 21 | 21 |
| DURO-TAK 87-2516 | 51.2 | 70.6 | 61.9 |
| Monoethanolamine | — | — | — |
| Diethanolamine | — | — | — |
| Triethanolamine | — | — | — |
| Isopropanolamine | — | — | — |
| Diisopropanolamine | 27.8 | — | — |
| Sodium hydroxide | — | 8.4 | — |
| Sodium acetate | — | — | 17.1 |
| Total | 100 | 100 | 100 |

(4) Measurement of Adhesion

For the adhesion of the obtained patch, the adhesion (before moisture absorption) and the adhesion (after moisture absorption) were calculated in the above described method and described in Table 5. "Rate of change (%)" in Table 5 refers to the value of adhesion of the adhesive layer after moisture adsorption when the value of adhesion of the adhesive layer before moisture absorption is taken as 100.

Figure 2:
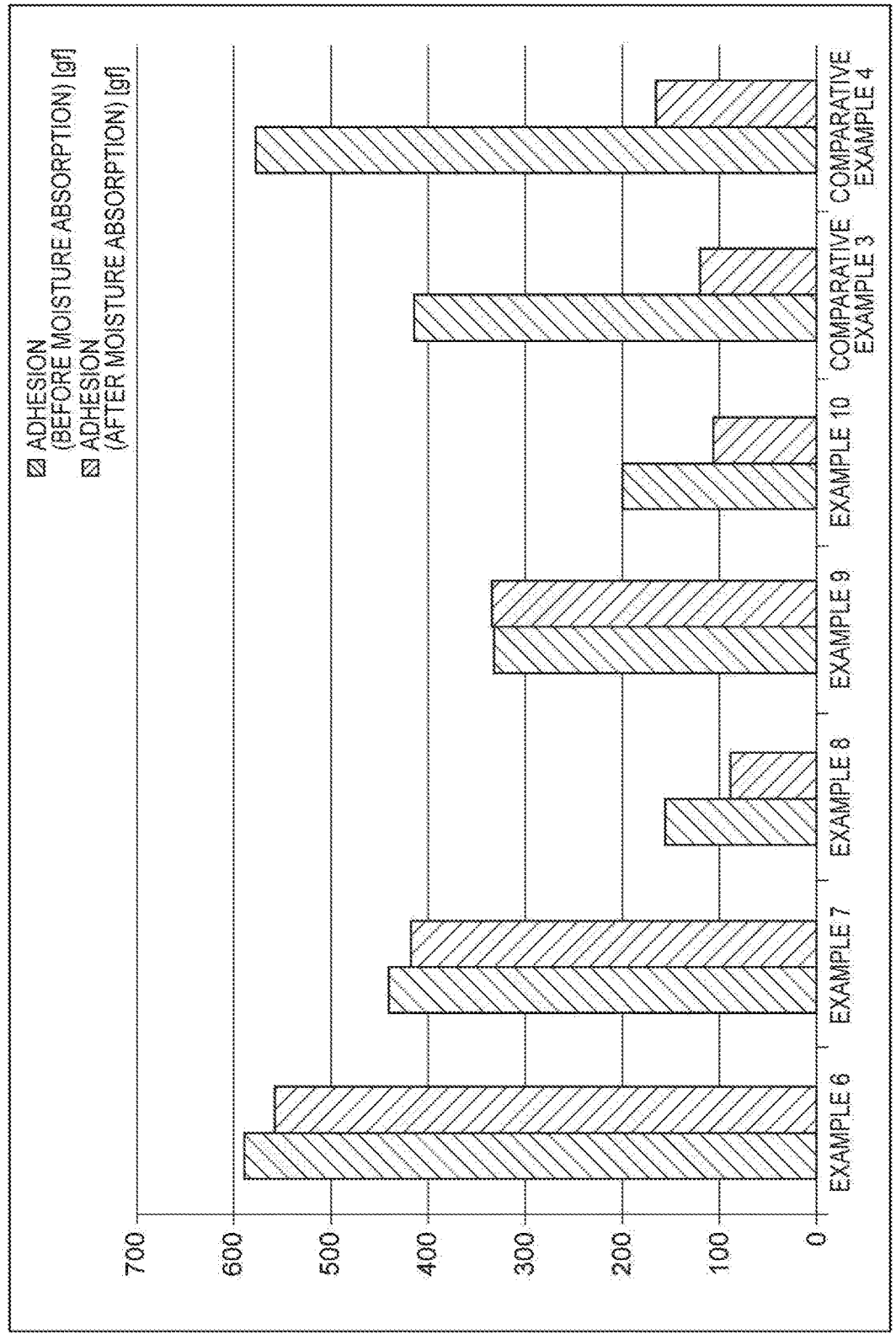
FIG. 2 is a graph showing the change in adhesion due to moisture absorption.

The result is shown in Table 5 and FIG. 2. The reduction of the adhesion of the patches of Examples 6 to 10 was less compared to that of the patches of Comparative Example 3 or 4 after the moisture absorption of the adhesive layers. In particular, the reduction of the adhesion of the patches of Examples 6, 7 and 9 was hardly observed.

TABLE 5

|  | Example 6 | Example 7 | Example 8 | Example 9 |
|---|---|---|---|---|
| Adhesion (before moisture absorption) [gf] | 593 | 441 | 153 | 329 |
| Adhesion (after moisture absorption) [gf] | 560 | 420 | 90 | 333 |
| Rate of change [%] | 94 | 95 | 59 | 101 |

|  | Example 10 | Comp. Example 3 | Comp. Example 4 |
|---|---|---|---|
| Adhesion (before moisture absorption) [gf] | 200 | 410 | 578 |
| Adhesion (after moisture absorption) [gf] | 107 | 116 | 160 |
| Rate of change [%] | 54 | 28 | 28 |

(5) Investigation of Amine

The reduction of the adhesion of the patches of Example 1 in which an equimolar amount of triethylamine, piperidine or quinuclidine was used instead of monoethanolamine (Examples 11 to 13, respectively) was also decreased same as other Examples. The reduction of the adhesion of the patches of Example 6 in which an equimolar amount of triethylamine, piperidine or quinuclidine was used instead of monoethanolamine (Examples 14 to 16, respectively) was also decreased same as other Examples.

The invention claimed is:

1. A patch, comprising:
   a backing; and
   an adhesive layer laminated on one side of the backing,
   wherein the adhesive layer comprises asenapine or a pharmaceutically acceptable salt thereof, an adhesive base comprising a rubber adhesive base, one or more low molecular weight amine, present in an amount of 0.5 to 40% by weight mass, selected from the group consisting of monoethanolamine, diethanolamine, triethanolamine, isopropanolamine and diisopropanolamine, a tackifier resin, liquid paraffin and a fatty acid ester having 6 to 20 carbon atoms, the adhesive layer exhibiting an effect of suppressing reduction of adhesion following moisture absorption;
   wherein the rubber adhesive base consists of styrene-isoprene-styrene block copolymer and polyisobutylene in a mass ratio ranging from 15:2 to 2:15.

2. A method of manufacturing a patch according to claim 1 comprising a backing and an adhesive layer laminated on one side of the backing, comprising:
   mixing asenapine or a pharmaceutically acceptable salt thereof, an adhesive base and a low molecular weight amine to obtain an adhesive composition; and
   laminating the adhesive composition on one side of the backing.

* * * * *